United States Patent
Diaz Martin et al.

(10) Patent No.: US 7,678,807 B2
(45) Date of Patent: Mar. 16, 2010

(54) ISOQUINOLINE AND BENZO[H] ISOQUINOLINE DERIVATIVES, PREPARATION AND THERAPEUTIC USE THEREOF AS ANTAGONISTS OF THE HISTAMINE H3 RECEPTOR

(75) Inventors: Juan Antonio Diaz Martin, Paris (FR); Beatriz Escribano Arenales, Paris (FR); Maria Dolores Jimenez Bargueno, Paris (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/122,795

(22) Filed: May 19, 2008

(65) Prior Publication Data

US 2008/0269199 A1 Oct. 30, 2008

Related U.S. Application Data

(63) Continuation of application No. PCT/EP2006/012246, filed on Nov. 22, 2006.

(30) Foreign Application Priority Data

Nov. 24, 2005 (EP) ................................. 05111248

(51) Int. Cl.
*A01N 43/42* (2006.01)
*A61K 31/44* (2006.01)
*C07D 221/18* (2006.01)
*C07D 221/22* (2006.01)

(52) U.S. Cl. .......................................... 514/279; 546/26
(58) Field of Classification Search ...................... None
See application file for complete search history.

(56) References Cited

U.S. PATENT DOCUMENTS

2007/0105834 A1 5/2007 Diaz Martin et al.

FOREIGN PATENT DOCUMENTS

| EP | 1070714 | 1/2001 |
| WO | WO 02/076925 | 10/2002 |
| WO | WO03076247 | * 9/2003 |

OTHER PUBLICATIONS

Vippagunta et al. Advanced Drug Delvivery Reviews, 2001, 48, 3-26.*

Grunewald et al, Examination of the Role of the Acidic Hydrogen in Imparting Selectivity of 7-(Aminosulfonyl)-1,2,3,4-tetrahydroisoquinoline (SK&F 29661) Toward Inhibition of Phenylethanolamine N-Methyltransferase vs the alpha2-Adrenoceptor, J. Med. Chem., 1997 (40) pp. 3997-4005.

Katritzky et al, 2-Substituted-1,2,3,4-tetrahydroisoquinolines and chiral 3-carboxyl analogues from N-benzotriazolylmethyl-N-phenethylamines, Tetrahedron: Asymmetry, 2001 (12) pp. 2427-2435.

Korte et al, Characterization and tissue Distribution of H3 Histamine Receptors in Guinea Pigs by N-alpha-Methylhistamine, Biochemical and Biophysical Research Communications, (1990) 168(3), pp. 979-986.

Liu et al, Does the [3H]Mepyramine Binding Site Represent the Histamine H1 Receptor? Re-examination of the Histamine H1 Receptor with Quinine, JPET, 1994 (268) 2, pp. 959-964.

Lovenberg et al, Cloning of Rat Histamine H3 Receptor Reveals Distinct Species Pharmacological Profiles, JPET (2000) 293, pp. 771-778.

Tozer et al, Histamine H3 Receptor Antagonists, Exp. Opin. Ther. Patents (2000) 10(7), pp. 1045-1055.

West, et al, Identification of Two H3-Histamine Receptor Subtypes, Molecular Pharmacology, 38, pp. 610-613, 1990.

* cited by examiner

*Primary Examiner*—James O Wilson
*Assistant Examiner*—Noble Jarrell
(74) *Attorney, Agent, or Firm*—Balaram Gupta; Kelly L. Bender

(57) ABSTRACT

The invention concerns a compound of formula (I):

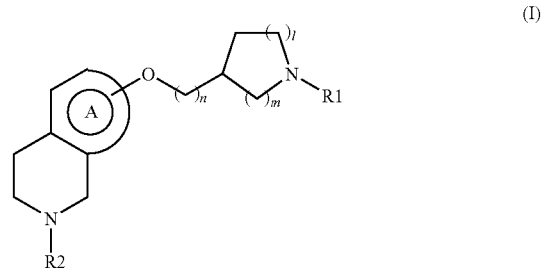

Wherein A, 1, m, n, R1 and R2 are as defined herein. The compounds of this invention are useful as medicaments, particularly, in the treatment of disorders improved by modulation of the histamine $H_3$ receptor.

18 Claims, No Drawings

ISOQUINOLINE AND BENZO[H] ISOQUINOLINE DERIVATIVES, PREPARATION AND THERAPEUTIC USE THEREOF AS ANTAGONISTS OF THE HISTAMINE H3 RECEPTOR

This application is a continuation of International application No. PCT/EP2006/012,246, filed Nov. 22, 2006, which is incorporated herein by reference in its entirety; which claims the benefit of priority of European Patent Application No. 05111248.0, filed Nov. 24, 2005.

A subject-matter of the present invention is ethers derived from tetrahydroisoquinoline and tetrahydrobenzo[H]isoquinoline, their process of preparation and their applications in therapeutics.

WO 02/076925 discloses histamine $H_3$ receptor antagonists. These compounds are, for some of the ether derivatives of isoquinolines or of benzoisoquinolines, ethers to which linear or cyclic alkylamines are attached.

The inventors were given the aim of achieving novel compounds which modulate the activity of the histamine $H_3$ receptor.

Consequently, a first subject-matter of the present invention is the novel compounds corresponding to the formula (I)

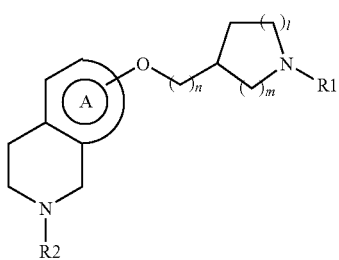

(I)

in which:

represents an unsaturated carbocycle with double bonds, such as a phenyl or a naphthyl; the carbocycle optionally being substituted by one or two substituents chosen, independently of one another, from a halogen atom, a hydroxyl, a nitro, cyano, $C_{1-2}$ perhaloalkyl or $C_{1-3}$ alkyl group or a phenyl;

l can take a value from 0 to 4;

m can take a value from 0 to 3;

n can take a value from 0 to 6;

—$(C)_l$—, —$(C)_m$— and —$(C)_n$— represent, independently of one another, a —$C_{x-z}$— alkylidene group, optionally substituted by 1 to 4 substituents chosen from a halogen atom, a hydroxyl, nitro, cyano, amino, $C_{1-2}$ perhaloalkyl or $C_{1-3}$ alkyl group or a phenyl; and, furthermore, when l, m and/or n takes the value 0, —$(C)_0$— represents a bond;

R1 represents a hydrogen atom, a $C_{1-3}$ alkyl group, a $C_{1-6}$ alkylcarbonyl, a $C_{1-6}$ alkoxycarbonyl, which can be substituted, these $C_{1-3}$ alkyl, $C_{1-6}$ alkylcarbonyl and $C_{1-6}$ alkoxycarbonyl groups, by a halogen atom, a hydroxyl, $C_{1-3}$ alkoxy, nitro, cyano or amino group or an aryl, such as a benzyloxycarbonyl; a $C_{1-3}$ alkylaryl, such as a benzyl or phenethyl, a monocyclic heteroaryl, such as a thienyl, furyl or pyrrolyl, or an aryl, such as a phenyl or a naphthyl; the aryl and heteroaryl groups optionally being substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group;

R2 represents a hydrogen atom or a $C_{1-6}$ alkyl or $C_{3-6}$ cycloalkyl group optionally substituted by 1 to 4 substituents chosen from a halogen atom, a hydroxyl, nitro, cyano, amino, $C_{1-3}$ monoalkylamino, $C_{2-6}$ dialkylamino, $C_{1-2}$ perhaloalkyl, $C_{1-3}$ haloalkyl, $C_{1-3}$ alkoxy or $C_{3-6}$ cycloalkyl group, a monocyclic heteroaryl, such as thienyl, furyl or pyrrolyl, a bicyclic heteroaryl, such as a benzotriazolyl, or an aryl group, such as a phenyl or a naphthyl; the aryl optionally being substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group.

In the context of the present invention:

$C_{x-z}$, where x and z can take the values from 0 to 6, is understood to mean a carbon chain which can have from x to z carbon atoms; however, when x takes the value 0, $C_0$ represents a bond; for example, $C_{1-6}$ indicates a carbon chain which can have from 1 to 6 carbon atoms; $C_{0-6}$ indicates a bond or a carbon chain which can have from 1 to 6 carbon atoms;

alkyl is understood to mean a saturated, linear or branched, aliphatic group; for example, a $C_{1-6}$ alkyl group represents a saturated, linear or branched, carbon chain having 1 to 6 carbon atoms, more particularly a methyl, ethyl, propyl, isopropyl, butyl, isobutyl or tert-butyl radical, and the like;

the term "$C_{x-y}$ alkylidene" or "$C_{x-y}$ alkylene" denotes a divalent, linear or branched, $C_{x-y}$ alkyl group; the term "$C_{2-8}$ alkenylidene" denoting a divalent, unsaturated, linear or branched, $C_{x-y}$ alkyl group;

$C_{x-y}$ alkoxy is understood to mean an alkyloxy group comprising a saturated, linear or branched, aliphatic chain comprising x to y carbon atoms;

halogen atom is understood to mean a fluorine, a chlorine, a bromine or an iodine;

$C_{1-3}$ monoalkylamino is understood to mean an amino monosubstituted by a $C_{1-3}$ alkyl group;

$C_{2-6}$ dialkylamino is understood to mean an amino disubstituted by two identical or different $C_{1-3}$ alkyl groups;

$C_{1-2}$ perhaloalkyl is understood to mean a $C_{1-2}$ alkyl group in which all the hydrogen atoms are substituted by a halogen atom;

$C_{1-3}$ haloalkyl is understood to mean a $C_{1-3}$ alkyl group in which at least one hydrogen atom is substituted by a halogen atom.

The compounds of formula (I) can comprise one or more asymmetric carbon atoms. They can also exist in the form of enantiomers or of diastereoisomers. These enantiomers, diastereoisomers and their mixtures, including their racemic mixtures, form part of the invention.

The compounds of general formula (I) can be provided in the form of free bases or of addition salts with acids, which also form part of the invention. These salts, according to the present invention, comprise those with pharmaceutically acceptable acids but also those with inorganic or organic acids which make possible suitable separation or crystallization of the compounds of formula (I). These salts can be prepared according to methods known to a person skilled in the art, for example by reaction of the compound of formula (I) in the base form with the acid in an appropriate solvent, such as an alcoholic solution or an organic solvent, then separation from the medium which comprises it by evaporation of the solvent or by filtration.

The compounds of formula (I) can also exist in the form of hydrates or of solvates, namely in the form of combinations with one or more water molecules or with a solvent. Such hydrates and solvates also form part of the invention.

Another subject-matter of the present invention is the compounds chosen from the following subgroups, considered alone or in combination, in which:

represents an unsaturated carbocycle, such as a phenyl or a naphthyl; the carbocycle optionally being substituted by 1 or 2 substituents chosen, independently of one another, from a halogen atom or a hydroxyl, nitro, cyano, $C_{1-2}$ perhaloalkyl or $C_{1-3}$ alkyl group;

l can take a value of 1, 2 or 3;

m can take a value of 0, 1 or 2;

n can take a value of 0, 1, 2 or 3;

—$(C)_l$— and —$(C)_m$— form, together with the —NR1- group, an aminocycle bonded via a carbon to the —O—$(C)_n$— group, such as azetidine, pyrrolidine, piperidine or azepine, and/or —$(C)_n$— represents a —$C_{0-3}$— alkylidene group optionally substituted by 1 to 4 substituents chosen from a halogen atom or a hydroxyl, nitro, cyano, amino or $C_{1-2}$ perhaloalkyl group; however, when n takes the value 0, —$(C)_0$— represents a bond;

R1 represents a hydrogen atom, a $C_{1-3}$ alkyl group, a $C_{1-4}$ alkylcarbonyl, a $C_{1-6}$ alkoxycarbonyl; $C_{1-3}$ alkylaryl, such as a benzyl, a heteroaryl, such as a thienyl or a furyl, an aryl group, such as a phenyl or a naphthyl; the aryl and heteroaryl groups optionally being substituted by 1 to 4 substituents chosen from a halogen atom or a hydroxyl, cyano, amino, $C_{1-3}$ monoalkylamino, $C_{1-3}$ alkyl, $C_{1-2}$ perhaloalkyl, $C_{1-3}$ haloalkyl, $C_{1-3}$ alkoxy or $C_{1-3}$ alkylidenedioxy group.

More particularly, when the aminocycle of which —$(C)_n$—, —$(C)_m$— and —NR1- form part and which is bonded via a carbon to the —O—$(C)_n$— group is chosen from the following groups:

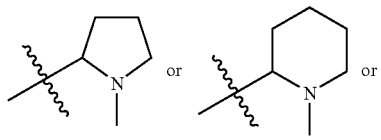

-continued

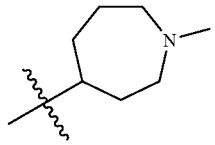

R2 represents a hydrogen atom or a $C_{1-4}$ alkyl or a $C_{5-6}$ cycloalkyl group optionally substituted by 1 to 4 substituents chosen from a phenyl, a monocyclic heteroaryl, such as a thienyl, a bicyclic heteroaryl, such as a benzotriazolyl, or a $C_{3-6}$ cycloalkyl, $C_{1-2}$ perhaloalkyl, $C_{1-3}$ haloalkyl or $C_{1-3}$ alkoxy group; the phenyl and the heteroaryl optionally being substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group.

Another subject-matter of the present invention relates to the following compounds and to their pharmaceutically acceptable salts:

Compound 1: 7-{2-[1-methylpiperidin-2-yl]ethoxy}-2-propyl-1,2,3,4-tetrahydroisoquinoline;

Compound 2: 2-isobutyl-7-[2-(1-methylpyrrolidin-2-yl)ethoxy]-1,2,3,4-tetrahydroisoquinoline;

Compound 3: 2-(3-methylbutyl)-7-[2-(1-methylpyrrolidin-2-yl)ethoxy]-1,2,3,4-tetrahydroisoquinoline;

Compound 4: 7-[(1-methylazepan-4-yl)oxy]-2-(3-methylbutyl)-1,2,3,4-tetrahydroisoquinoline;

Compound 5: 2-(cyclohexylmethyl)-7-[2-(1-methylpyrrolidin-2-yl)ethoxy]-1,2,3,4-tetrahydroisoquinoline;

Compound 6: 2-(cyclohexylmethyl)-7-{2-[(2R)-1-methylpyrrolidin-2-yl]ethoxy}-1,2,3,4-tetrahydroisoquinoline;

Compound 7: 2-(cyclohexylmethyl)-7-{2-[(2S)-1-methylpyrrolidin-2-yl]ethoxy}-1,2,3,4-tetrahydroisoquinoline;

Compound 8: 2-(cyclohexylmethyl)-7-[(1-methylazepan-4-yl)oxy]-1,2,3,4-tetrahydroisoquinoline;

Compound 9: 2-(cyclohexylmethyl)-7-[2-(1-methylpiperidin-2-yl)ethoxy]-1,2,3,4-tetrahydroisoquinoline;

Compound 10: 2-benzyl-7-[2-(1-methylpyrrolidin-2-yl)ethoxy]-1,2,3,4-tetrahydroisoquinoline;

Compound 11: 2-benzyl-7-[(1-methylazepan-4-yl)oxy]-1,2,3,4-tetrahydroisoquinoline;

Compound 12: 7-[(1-methylazepan-4-yl)oxy]-2-(2-thienylmethyl)-1,2,3,4-tetrahydroisoquinoline;

Compound 13: 2-(cyclohexylmethyl)-8-[2-(1-methylpyrrolidin-2-yl)ethoxy]-1,2,3,4-tetrahydrobenzo[h]isoquinoline;

Compound 14: 2-(cyclohexylmethyl)-8-{2-[(2R)-1-methylpyrrolidin-2-yl]ethoxy}-1,2,3,4-tetrahydrobenzo[h]isoquinoline;

Compound 15: 2-(cyclohexylmethyl)-8-{2-[(2S)-1-methylpyrrolidin-2-yl]ethoxy}-1,2,3,4-tetrahydrobenzo[h]isoquinoline;

Compound 16: 2-(cyclohexylmethyl)-8-[(1-methylazepan-4-yl)oxy]-1,2,3,4-tetrahydrobenzo[h]isoquinoline;

Compound 17: 2-(cyclohexylmethyl)-8-[2-(1-methylpiperidin-2-yl)ethoxy]-1,2,3,4-tetrahydrobenzo[h]isoquinoline;

Compound 20: 2-butyl-7-[(1-methylazepan-4-yl)oxy]-1,2,3,4-tetrahydroisoquinoline;

Compound 21: 2-butyl-7-[2-(1-methylpyrrolidin-2-yl)ethoxy]-1,2,3,4-tetrahydroisoquinoline;

Compound 22: 7-[(1-methylazepan-4-yl)oxy]-2-propyl-1,2,3,4-tetrahydroisoquinoline;

Compound 23: 7-[2-(1-methylpyrrolidin-2-yl)ethoxy]-2-propyl-1,2,3,4-tetrahydroisoquinoline.

Furthermore, in the context of the present invention, the term "protective group Pg" is understood to mean a group which makes it possible, on the one hand, to protect a reactive functional group, such as a hydroxyl or an amine, during a synthesis and, on the other hand, to regenerate the intact reactive functional group at the end of synthesis. Examples of protective groups and protecting and deprotecting methods are given in "Protective Groups in Organic Synthesis", 3$^{rd}$ Ed., Greene and Wuts (John Wiley & Sons Inc., New York, 1999).

A second subject-matter of the present invention is a process for the preparation of the compounds of formula (I) according to the invention.

Thus, the compounds of formula (I) can be prepared according to the process represented in Scheme 1.

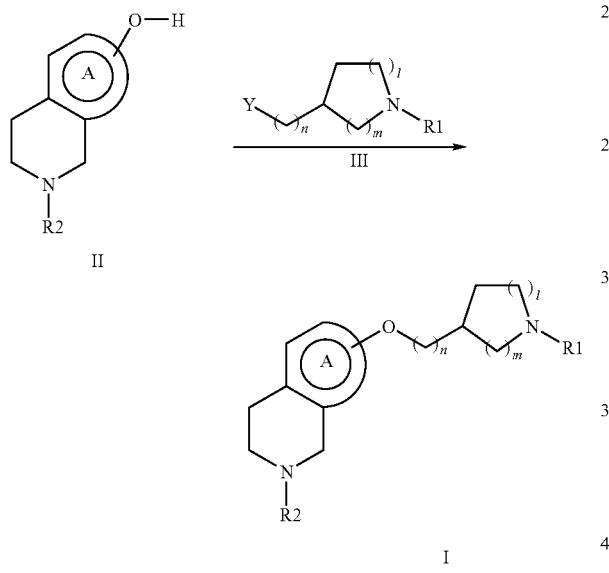

According to the process of Scheme 1, the compounds of formula (I), in which R1, R2, l, m, n and the A ring are as defined in the formula (I), are prepared by nucleophilic substitution by reacting a phenol of formula (II), in which R2 and the A ring are as defined in the formula (I), with an amine of formula (III), in which R1, l, m and n are defined as in the formula (I) and Y represents a halogen atom, such as, for example, a chlorine, iodine or bromine, or represents a "pseudohalogen", such as a mesylate, triflate, tosylate, brosylate or nosylate. The reaction can be carried out in a protic or aprotic solvent, such as water, methanol, acetone, butanone, ethyl acetate, toluene, N,N-dimethylformamide, acetonitrile or a mixture of these solvents, at a temperature of between 0 and 110° C. in the presence of a base, such as, for example, sodium hydroxide, potassium hydroxide, sodium carbonate, potassium carbonate, triethylamine or diisopropylethylamine, to give the compound of formula (I). In the case of the mixtures of immiscible solvents, use may be made of a phase transfer catalyst, such as an ammonium or phosphonium salt, preferably tetrabutylammonium bromide or tetraethylammonium chloride, in a mixture of toluene and water at a temperature of between 20 and 110° C. If necessary, the compounds of the formulae (II) and (III) can be protected beforehand before reaction according to methods known to a person skilled in the art. The compound of formula (I) is then optionally deprotected according to conditions known to a person skilled in the art.

Alternatively, the compounds of formula (I) can be prepared according to a reaction of Mitsunobu type. According to this alternative, a phenol of formula (II), in which R2 and the A ring are as defined in the formula (I), is reacted with an amine of formula (III), in which R1, l, m and n are defined as in the formula (I) but Y represents a hydroxyl group, obtained according to methods known to a person skilled in the art. The reaction can be carried out conventionally in the presence of Mitsunobu reagents, such as an azo derivative, for example diethyl azodicarboxylate, diisopropyl azodicarboxylate, di(tert-butyl) azodicarboxylate, 1,1'-(azodicarbonyl)dipiperidine or Ia N,N,N',N'-tetramethylazodicarboxamide, and a phosphine, for example triphenylphosphine or tributylphosphine. The reaction can be carried out in an aprotic solvent, such as tetrahydrofuran or dioxane or a mixture of these solvents, at a temperature of between 0 and 100° C. to give the compound of formula (I). The compound of formula (I), if the reactants have had to be protected beforehand before reaction, is deprotected according to conditions known to a person skilled in the art.

The protective starting compounds (formula (VI)) or the unprotected starting compounds (formula (II)) can be prepared according to Scheme 2 or can be synthesized by conventional methods known to a person skilled in the art, such as the Journal of Medicinal Chemistry, 40, 3997-4005 (1997) or Tetrahedron Asymmetry, 12, 2427-2434 (2001).

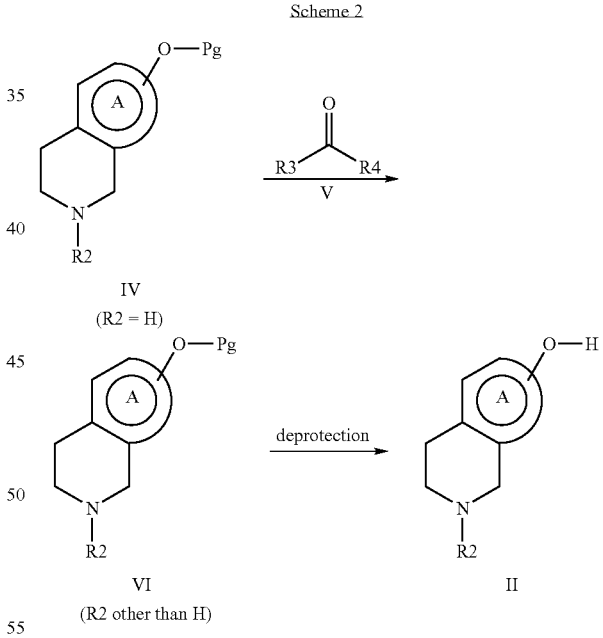

According to the process of Scheme 2, the compounds of formula (II), in which R2 is as defined in the formula (I) but other than a hydrogen atom, are prepared by reductive amination by reacting a secondary amine of formula (IV), in which R2 represents H, with an aldehyde or a ketone of formula (V), where R3 and R4, after reaction, together form R2 as defined in the formula (I) and other than hydrogen. The compounds of formula (IV), where R2 represents a hydrogen atom, can be obtained according to conventional methods known to a person skilled in the art, such as the Journal of Medicinal Chemistry, 40, 3997-4005 (1997). The compounds of formula (II) can subsequently be obtained from the compounds of formula (VI), which are deprotected according to conditions known to a person skilled in the art. For example, the compounds of formula (VI), when Pg is a methyl group, can be deprotected in the presence of an acid, such as hydrobromic acid, in a protic solvent, such as water or acetic acid or a mixture of these solvents, at a temperature of between 0 and 100° C. in the presence or absence of a phase transfer catalyst, such as an ammonium or phosphonium salt, to give the phenol of formula (II). Illustrations of the process are given in the examples.

Alternatively, according to the process of Scheme 3, the compounds of formula (II), in which R2 is as defined in the formula (I) but other than a hydrogen atom, can be prepared by reacting the protective compound of formula (VI), in which R2 represents a benzotriazolylmethyl group, for example obtained according to the process described in Tetrahedron Asymmetry, 12, 2427-2434 (2001), with an alkylating agent, such as an appropriate Grignard reagent.

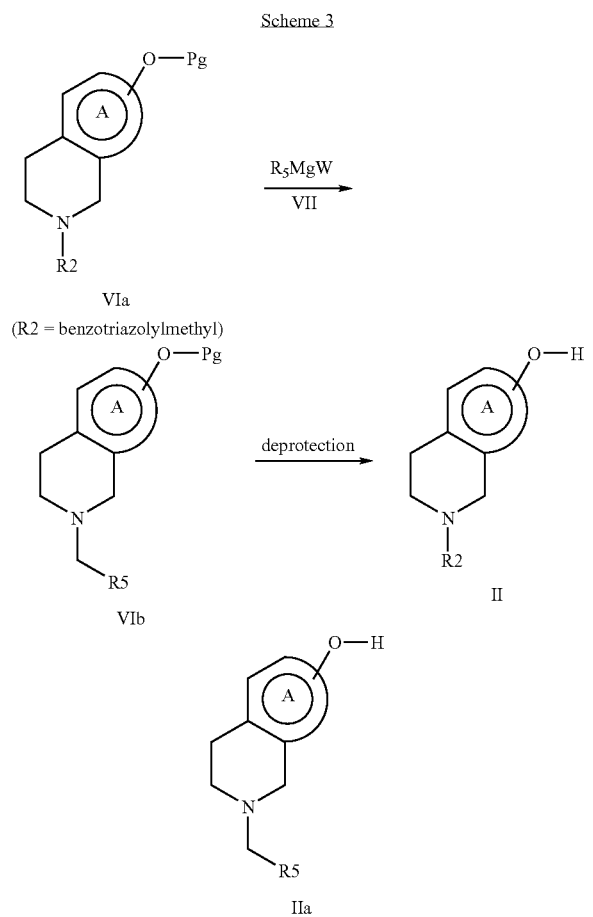

According to this alternative, the compounds of formula (II), in which R2 is as defined in the formula (I), are prepared by nucleophilic substitution by reacting a compound of formula (VIa), in which R2 represents a benzotriazolylmethyl group, with a Grignard reagent of formula (VII), where W represents a halogen atom, such as, for example, a chlorine, iodine or bromine, and R5 represents a $C_{1-5}$ alkyl, $C_{1-2}$ perhaloalkyl, $C_{1-3}$ haloalkyl or $C_{3-6}$ cycloalkyl group, a monocyclic heteroaryl, such as a thienyl or furyl, or an aryl group, such as a phenyl or a naphthyl; after reaction, the compound of formula (II), where R2 is as defined in the formula (I) and is other than hydrogen, is formed. The reaction can be carried out in an aprotic solvent, such as diethyl ether, tetrahydrofuran or dioxane or a mixture of these solvents, at a temperature of between −70 and 100° C., to give the compound of formula (VI). The compounds of formula (II) can subsequently be obtained from the compounds of formula (VI), which are deprotected according to conditions known to a person skilled in the art. For example, the compounds of formula (VI), when Pg is a methyl group, can be deprotected in the presence of an acid, such as hydrobromic acid, in a protic solvent, such as water or acetic acid or a mixture of these solvents, at a temperature of between 0 and 100° C. in the presence or absence of a phase transfer catalyst, such as an ammonium or phosphonium salt, to give the phenol of formula (II). Illustrations of the process are given in the examples.

The starting compounds II and the amines of formula (III) are directly available commercially or can be synthesized by methods described such as beforehand, by conventional methods known to a person skilled in the art or are known in the literature.

According to another of its aspects, a subject-matter of the invention is medicaments which comprise a compound of formula (I) or an addition salt of the latter with a pharmaceutically acceptable acid or also a hydrate or a solvate of the compound of formula (I).

These compounds of the present invention are employed in therapeutics, in particular the treatment of disorders improved by modulation of the histamine $H_3$ receptor and in the treatment of pathologies in which an antagonist of the histamine $H_3$ receptor is of therapeutic benefit. Such pathologies are in particular obesity and diabetes.

These compounds with properties as antagonist and inverse agonist of the histamine $H_3$ receptor are also useful in the treatment of diseases of the central nervous system.

These compounds can also be employed in the treatment of diseases of the central nervous system, such as watchfulness and sleep disorders, narcolepsy, Alzheimer's disease and other types of dementia, Parkinson's disease, attention disorders in hyperkinetic children, memory and learning disorders, epilepsy, schizophrenia, moderate cognitive disorders, depression and anxiety. The states of depression and of anxiety comprise, for example, anticipatory anxiety (before a surgical operation, before dental treatment, and the like), anxiety caused by dependence on or weaning from alcohol or drugs, mania, seasonal affective disorder, migraine and nausea. They can also be used in the treatment of sexual dysfunction, dizziness and travel sickness.

The use of the compounds according to the invention in the preparation of a medicament intended to treat the abovementioned pathologies forms an integral part of the invention.

According to another of its aspects, the present invention relates to pharmaceutical compositions comprising, as active principle, at least one compound according to the invention. These pharmaceutical compositions comprise an effective dose of at least one compound according to the invention, or a pharmaceutically acceptable salt, a hydrate or a solvate of the said compound, and at least one or more pharmaceutically acceptable excipients. Said excipients are chosen, according to the pharmaceutical form and the method of administration desired, from the normal excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its optional salt, solvate or hydrate can be administered in unit administration form, as a mixture with conventional pharmaceutical excipients, to animals and to human beings, for the prophylaxis or the treatment of the above disorders or diseases.

The appropriate unit administration forms comprise oral forms, such as tablets, soft or hard gelatin capsules, powders, granules and oral solutions or suspensions, sublingual, buccal, intratracheal or intranasal administration forms, forms for administration by inhalation, topical, transdermal, subcutaneous, intramuscular or intravenous administration forms, rectal administration forms and implants. For the topical application, the compounds according to the invention can be used in creams, gels, ointments or lotions.

In order to obtain the desired prophylactic or therapeutic effect, the dose of active principle can vary between 0.1 μg and 50 mg per kg of body weight and per day. Each unit dose can comprise from 0.1 to 1000 mg, preferably from 1 to 500 mg, of active principle, in combination with a pharmaceutical excipient. This unit dose can be administered 1 to 5 times daily, so as to administer a daily dosage on 0.5 to 5000 mg, preferably of 1 to 2500 mg.

There may be particular cases where higher or lower dosages are appropriate. Such dosages are also within the scope of this invention. According to the usual practice, the dosage appropriate to each patient is determined by the physician according to the method of administration and the weight and response of the said patient.

By way of example, a unit administration form of a compound according to the invention is comprised of:

| | |
|---|---:|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

The present invention, according to another of its aspects, also relates to a method for the treatment of the pathologies indicated above which comprises the administration, to a patient, of an effective dose of a compound according to the invention or one of its pharmaceutically acceptable salts or its hydrates or solvates.

The following examples illustrate the processes and techniques appropriate for the preparation of this invention, without, however, limiting the extent of its scope.

EXAMPLE 1

2-(Cyclohexylmethyl)-7-[2-(1-methylpyrrolidin-2-yl)ethoxy]-1,2,3,4-tetrahydroisoquinoline oxalate (1:2)

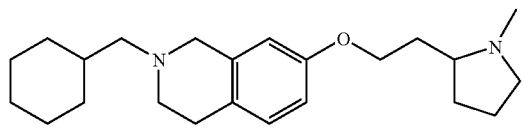

1.1—2-(cyclohexylmethyl)-7-methoxy-1,2,3,4-tetrahydroisoquinoline 35 ml (0.070 mol) of a 2N solution of cyclohexylmagnesium chloride in tetrahydrofuran are added to a solution, cooled to −40° C., of 10.41 g (0.035 mol) of 2-(1H-1,2,3-benzotriazol-1-ylmethyl)-7-methoxy-1,2,3,4-tetrahydroisoquinoline in 150 ml of tetrahydrofuran. Stirring is maintained at −40° C. for 2 hours and then the mixture is left to stand overnight at ambient temperature. An aqueous solution of a 2N sodium hydroxide solution (50 ml) is added. The aqueous phase is extracted 3 times with 20 ml of ethyl ether and the organic phases are dried and evaporated to dryness under vacuum. 8.20 g of oil are obtained, which oil is used without additional purification.

Yd: 90%

M.p.=oil 1.2—2-(cyclohexylmethyl)-1,2,3,4-tetrahydroisoquinolin-7-ol hydrobromide A solution of 8.20 g (0.032 mol) of 2-(cyclohexylmethyl)-7-methoxy-1,2,3,4-tetrahydroisoquinoline in 80 ml of aqueous hydrogen bromide (48%) is heated at 120° C. for 6 hours. The mixture is cooled and concentrated to dryness, and the residue is treated with 60 ml of an ethanol/ethyl ether mixture. The solid which has been formed is filtered off, washed with ethyl ether and dried. 9.70 g of the desired product are obtained as a pure white solid.

Yd: 94%

M.p.=210-214° C.

1.3—2-(Cyclohexylmethyl)-7-[2-(1-methylpyrrolidin-2-yl)ethoxy]-1,2,3,4-tetrahydroisoquinoline oxalate (1:2)

A mixture of 9.7 g (0.244 mol) of sodium hydroxide in 125 ml of water is added to a mixture of 5.00 g (0.020 mol) of the compound obtained above in 1.2, 11.2 g (0.0061 mol) of 2-(2-chloroethyl)-1-methylpyrroline and 0.41 g (0.002 mol) of tetraethylammonium chloride in 125 ml of toluene. The reaction mixture is heated at reflux for 8 hours. The phases are separated and the aqueous phase is extracted twice with 20 ml of toluene. The organic phases are dried and then evaporated to dryness. 7 g (97%) of a crude oil are obtained, which oil is purified by chromatography on a column of silica gel with a dichloromethane/methanol (98:2) mixture employed as eluent. The desired product (0.70 g; 10%) is obtained in the form of an oil with the greatest $R_f$.

$^1$H NMR (CDCl$_3$) δ (ppm): 7.1 (1H, d), 6.7 (1H, d), 6.5 (1H, s), 4.0 (2H, m), 3.5 (2H, s), 3.0 (1H, m), 2.7 (2H, m), 2.6 (2H, m), 2.4 (3H, s), 2.2 (2H, d), 2.1 (2H, m) 2.0 (1H, m), 1.7 (11H, m), 1.1 (3H, m), 0.9 (2H, m).

The preceding oil (0.65 g, 0.002 mol) is dissolved in 10 ml of ethanol and then 0.36 g (0.004 mol) of oxalic acid, dissolved in 10 ml of ethanol, is added. The precipitate is filtered off and washed with cold ethanol. 0.46 g of the desired product is obtained as a white solid.

Yd: 47%

M.p.=78-98° C.

EXAMPLE 2

2-(Cyclohexylmethyl)-7-[(1-methylazepan-4-yl)oxy]-1,2,3,4-tetrahydroisoquinoline oxalate (1:2)

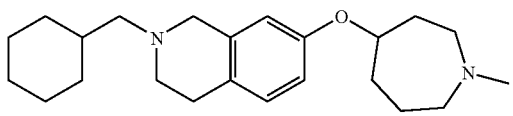

An oil of the smallest $R_f$ obtained is obtained (1.30 g, 0.002 mol) according to the process described above in 1.3 which corresponds to the structure of 2-(cyclohexylmethyl)-7-[(1-methylazepan-4-yl)oxy]-1,2,3,4-tetrahydroisoquinoline.

$^1$H NMR (CDCl$_3$) δ (ppm): 7.1 (1H, d), 6.7 (1H, d), 6.5 (1H, s), 4.5 (1H, m), 3.5 (2H, s), 2.7 (2H, m), 2.6-2.4 (5H, m), 2.3 (3H, s), 2.2 (2H, d), 2.0 (2H, m), 1.7 (11H, m), 1.1 (3H, m), 0.9 (2H, m).

The oil is dissolved in 12 ml of ethanol and then 0.24 g (0.003 mol) of oxalic acid, dissolved in 12 ml of ethanol, is added. The precipitate is filtered off and washed with cold ethanol. 0.46 g of the desired product is obtained as a white solid.

Yd: 86%
M.p.=110-112° C.

EXAMPLE 3

2-(Cyclohexylmethyl)-8-[2-(1-methylpyrrolidin-2-yl)ethoxy]-1,2,3,4-tetrahydrobenzo[h]isoquinoline oxalate (2:1)

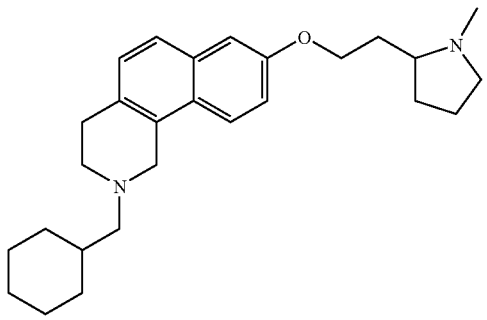

3.1—2-(cyclohexylmethyl)-8-methoxy-1,2,3,4-tetrahydroisobenzo[h]quinoline 0.32 g (0.0003 mol) of 10% palladium-on-charcoal is added to a solution of 3 g (0.014 mol) of 8-methoxy-1,2,3,4-tetrahydroisobenzo[h]quinoline and 1.6 g (0.014 mol) of cyclohexanecarboxaldehyde in 70 ml of methanol. The solution is hydrogenated for 24 hours in a Paar hydrogenator at a pressure of 45 psi. The catalyst is removed by filtration and the filtered solution is evaporated to dryness. 4 g of the desired product are obtained as an oil.

Yd: 93%
M.p.: oil

3.2—2-(Cyclohexylmethyl)-1,2,3,4-tetrahydrobenzo[h]isoquinolin-7-ol hydrobromide A solution of 2 g (0.006 mol) of 2-(cyclohexylmethyl)-8-methoxy-1,2,3,4-tetrahydroisobenzo[h]quinoline in 30 ml of aqueous hydrogen bromide (48%) is heated at 120° C. for 6 hours. The mixture is cooled and concentrated to dryness, and the residue is treated with 20 ml of an ethanol/ethyl ether mixture. The solid which was formed is filtered off, washed with ethyl ether and dried. 2.3 g of the desired product are obtained as a pure white solid.

Yd: 96%
M.p.=270-276° C.

3.3—2-(Cyclohexylmethyl)-8-[2-(1-methylpyrrolidin-2-yl)ethoxy]-1,2,3,4-tetrahydrobenzo[h]isoquinoline oxalate (1:2)

A mixture of 2.5 g (0.064 mol) of sodium hydroxide in 75 ml of water is added to a mixture of 2.00 g (0.005 mol) of the compound obtained above in 3.2, 2.4 g (0.014 mol) of 2-(2-chloroethyl)-1-methylpyrroline and 0.11 g (0.0006 mol) of tetraethylammonium chloride in 75 ml of toluene. The reaction mixture is heated at reflux for 8 hours. The phases are separated and the aqueous phase extracted twice with 20 ml of toluene. The organic phases are dried and then evaporated to dryness. 3 g (>100%) of a brown oil are obtained, which oil is purified by chromatography on a column of silica gel with a dichloromethane/methanol (98:2) mixture employed as eluent. The desired product (0.70 g; 10%) is obtained in the form of an oil with the greatest $R_f$.

$^1$H NMR (CDCl$_3$) δ (ppm): 7.7 (1H, d), 7.5 (1H, d), 7.1-7.0 (3H, m), 4.2 (2H, m), 4.0 (2H, s), 3.0 (1H, m), 2.9 (2H, m), 2.7 (2H, m), 2.4 (2H, d), 2.3 (3H, s), 2.2-2.0 (3H, m), 1.7 (11H, m), 1.1 (3H, m), 0.9 (2H, m).

The preceding oil (0.5 g, 0.001 mol) is dissolved in 10 ml of ethanol and then 0.24 g (0.003 mol) of oxalic acid, dissolved in 10 ml of ethanol, is added. The precipitate is filtered off and washed with cold ethyl ether to produce 0.50 g of the desired product as a white solid.

Yd: 70%
M.p.=127-135° C.

EXAMPLE 4

2-(Cyclohexylmethyl)-8-[(1-methylazepan-4-yl)oxy]-1,2,3,4-tetrahydrobenzo[h]isoquinoline oxalate (1:2)

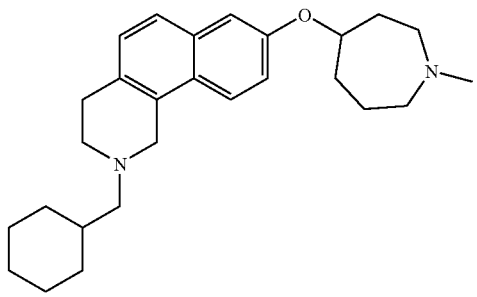

An oil with the smallest $R_f$ obtained is obtained (0.67 g, 0.002 mol) according to the process described above in 3.3 which corresponds to the structure of 2-(cyclohexylmethyl)-7-[(1-methylazepan-4-yl)oxy]-1,2,3,4-tetrahydroisoquinoline $^1$H NMR (CDCl$_3$) δ (ppm): 7.8 (1H, d), 7.6 (1H, d), 7.2-7.0 (3H, m), 4.7 (1H, m), 4.0 (2H, s), 3.0 (2H, m), 2.9 (2H, m), 2.7 (2H, m), 2.4 (2H, d), 2.3 (3H, s), 2.3-1.7 (14H, m), 1.1 (3H, m), 0.9 (2H, m).

The oil is dissolved in 10 ml of ethanol and then 0.37 g (0.004 mol) of oxalic acid, dissolved in 10 ml of ethanol, is added. The precipitate is filtered off and washed with cold ethyl ether to produce 0.25 g of the desired product as a white solid.

Yd: 31%

M.p.=77-101° C.

EXAMPLE 5

2-(Cyclohexylmethyl)-7-(2-[(2S)-1-methylpyrrolidin-2-yl]ethoxy)-1,2,3,4-tetrahydroisoquinoline hydrochloride (1:2)

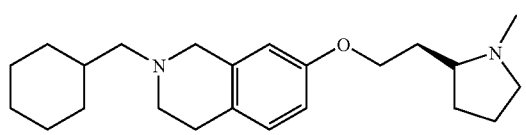

6.6 g (0.032 mol) of diisopropyl azodicarboxylate are added to a mixture, cooled to −5° C., of 7.3 g (0.030 mol) of 2-(cyclohexylmethyl)-1,2,3,4-tetrahydroisoquinolin-7-ol obtained above in 1.2, 3.5 g (0.027 mol) of (S)-2-(2-hydroxyethyl)-1-methylpyrroline and 9.2 g (0.036 mol) of triphenylphosphine in 150 ml of tetrahydrofuran. Stirring is maintained overnight at ambient temperature. The solution is evaporated to dryness and a crude oil is obtained which is purified by chromatography on a column of silica gel with a dichloromethane/methanol (95:5) mixture employed as eluent. The desired product (1.4 g; 15%) is obtained in the form of an oil.

$^1$H NMR (CDCl$_3$) δ (ppm): 7.1 (1H, d), 6.7 (1H, d), 6.5 (1H, s), 4.0 (2H, m), 3.5 (2H, s), 3.0 (1H, m), 2.7 (2H, m), 2.6 (2H, m), 2.4 (3H, s), 2.2 (2H, d), 2.1 (2H, m) 2.0 (1H, m), 1.7 (11H, m), 1.1 (3H, m), 0.9 (2H, m).

The oil is dissolved in 25 ml of isopropanol and then isopropanol is saturated with HCl. The precipitate is filtered off and washed with 1 ml of cold isopropanol. 1 g of the desired product is obtained as a white solid.

Yd: 59%

M.p.=238-241° C.

EXAMPLE 6

2-(Cyclohexylmethyl)-8-[(2S)-(1-methylpyrrolidin-2-yl)ethoxy]-1,2,3,4-tetrahydrobenzo[h]isoquinoline hydrochloride (1:2)

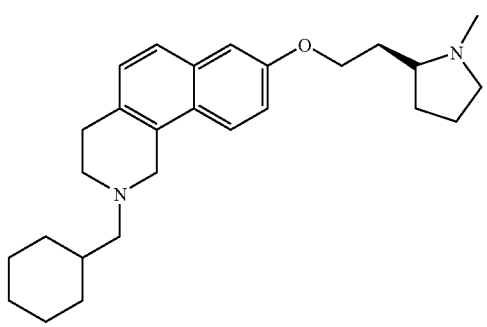

1.88 g (0.008 mol) of diisopropyl azodicarboxylate are added to a mixture, cooled to −5° C., of 2.2 g (0.007 mol) of the 2-(cyclohexylmethyl)-1,2,3,4-tetrahydrobenzo[h]isoquinolin-7-ol compound obtained above in 3.2, 0.95 g (0.007 mol) of (S)-2-(2-hydroxyethyl)-1-methylpyrroline and 2.14 g (0.008 mol) of triphenylphosphine in 150 ml of tetrahydrofuran. Stirring is maintained at ambient temperature overnight. The solution is evaporated to dryness and a crude oil is obtained which is purified by chromatography on a column of silica gel with a dichloromethane/methanol (95:5) mixture employed as eluent. The desired product (1.1 g; 36%) is obtained in the form of an oil.

$^1$H NMR (CDCl$_3$) δ (ppm): 7.7 (1H, d), 7.5 (1H, d), 7.1-7.0 (3H, m), 4.2 (2H, m), 4.0 (2H, s), 3.0 (1H, m), 2.9 (2H, m), 2.7 (2H, m), 2.4 (2H, d), 2.3 (3H, s), 2.2-2.0 (3H, m), 1.7 (11H, m), 1.1 (3H, m), 0.9 (2H, m).

The oil is dissolved in 15 ml of isopropanol and then isopropanol is saturated with HCl. The precipitate is filtered off and washed with 1 ml of cold isopropanol. 0.8 g of the desired product is obtained as a white solid.

Yd: 62%

M.p.=260° C.

The chemical structures and the physical properties of a few compounds according to the invention are illustrated in the following table. The elemental microanalyses and the NMR, IR and mass spectra confirm the structures of the compounds obtained.

In the table, for the compounds of formula (I), "M.p." corresponds to the melting point and "Config." indicates the stereochemical configuration, namely (R), (S) or a racemic mixture (R,S), of the carbon atom indicated by the asterix (*).

TABLE (I)

| No. | R2 | R1 | A | n | m | l | Config. | M.p. (° C.) | Salt |
|---|---|---|---|---|---|---|---|---|---|
| 1. | n-butyl | CH₃ | benzene (1,2,4-trisub) | 2 | 0 | 3 | (R,S) | 186-190 | Hydrochloride |
| 2. | isobutyl | CH₃ | benzene (1,2,4-trisub) | 2 | 0 | 2 | (R,S) | 77-80 | Tartrate |
| 3. | isopentyl | CH₃ | benzene (1,2,4-trisub) | 2 | 0 | 2 | (R,S) | 61-65 | Tartrate |
| 4. | isopentyl | CH₃ | benzene (1,2,4-trisub) | 0 | 2 | 2 | (R,S) | 60-70 | Tartrate |
| 5. | cyclohexylmethyl | CH₃ | benzene (1,2,4-trisub) | 2 | 0 | 2 | (R,S) | 78-98 | Oxalate |

TABLE-continued (I)

| No. | R2 | R1 | A | n | m | l | Config. | M.p. (° C.) | Salt |
|---|---|---|---|---|---|---|---|---|---|
| 6. | cyclohexylmethyl | CH₃ | 1,2,4-trisubstituted benzene | 2 | 0 | 2 | (R) | 190-200 | Hydrochloride |
| 7. | cyclohexylmethyl | CH₃ | 1,2,4-trisubstituted benzene | 2 | 0 | 2 | (S) | 195-199 | Oxalate |
| 8. | cyclohexylmethyl | CH₃ | 1,2,4-trisubstituted benzene | 0 | 2 | 2 | (R,S) | 110-112 | Oxalate |
| 9. | cyclohexylmethyl | CH₃ | 1,2,4-trisubstituted benzene | 2 | 0 | 3 | (R,S) | 101-111 | Oxalate |
| 10 | benzyl | CH₃ | 1,2,4-trisubstituted benzene | 2 | 0 | 2 | (R,S) | 143-150 | Oxalate |

TABLE-continued (I)

| No. | R2 | R1 | A | n | m | l | Config. | M.p. (° C.) | Salt |
|---|---|---|---|---|---|---|---|---|---|
| 11 | benzyl | CH₃ | 1,2,4-trisubstituted benzene | 0 | 2 | 2 | (R,S) | 108-116 | Oxalate |
| 12 | thiophen-2-ylmethyl | CH₃ | 1,2,4-trisubstituted benzene | 0 | 2 | 2 | (R,S) | 98-110 | Oxalate |
| 13 | cyclohexylmethyl | CH₃ | 1,2,6-trisubstituted naphthalene | 2 | 0 | 2 | (R,S) | 127-135 | Oxalate |
| 14 | cyclohexylmethyl | CH₃ | 1,2,6-trisubstituted naphthalene | 2 | 0 | 2 | (R) | 274-277 | Hydrochloride |
| 15 | cyclohexylmethyl | CH₃ | 1,2,6-trisubstituted naphthalene | 2 | 0 | 2 | (S) | 271-274 | Oxalate |

TABLE-continued (I)

| No. | R2 | R1 | A | n | m | l | Config. | M.p. (° C.) | Salt |
|---|---|---|---|---|---|---|---|---|---|
| 16 | cyclohexylmethyl | CH₃ | naphthalene-2,6-diyl | 0 | 2 | 2 | (R,S) | 77-82 | Oxalate |
| 17 | cyclohexylmethyl | CH₃ | naphthalene-2,6-diyl | 2 | 0 | 3 | (R,S) | 124-127 | Oxalate |
| 18 | cyclohexylmethyl | CH₃ | phenylene | 2 | 0 | 2 | (S) | 238-241 | Hydrochloride |
| 19 | cyclohexylmethyl | CH₃ | naphthalene-2,6-diyl | 2 | 0 | 2 | (S) | 260 | Hydrochloride |
| 20 | n-pentyl | CH₃ | phenylene | 0 | 2 | 2 | (R;S) | 96-107 | Tartrate |

TABLE-continued (I)

| No. | R2 | R1 | A | n | m | l | Config. | M.p. (° C.) | Salt |
|---|---|---|---|---|---|---|---|---|---|
| 21 | pentyl | CH$_3$ | 1,2,4-trisubstituted phenyl | 2 | 0 | 2 | (R,S) | 95-105 | Tartrate |
| 22 | butyl | CH$_3$ | 1,2,4-trisubstituted phenyl | 0 | 2 | 2 | (R,S) | 76-97 | Tartrate |
| 23 | butyl | CH$_3$ | 1,2,4-trisubstituted phenyl | 2 | 0 | 2 | (R,S) | 66-91 | Tartrate |

The compounds of the invention of formula (I) have formed the subject of pharmacological tests which have shown their advantage as therapeutically active substances.

More particularly, the compounds of the invention are histamine H$_3$ receptor antagonists. H$_3$ receptors are known to a person skilled in the art and their therapeutic advantage has been described in the literature ("Histamine H$_3$ Receptor Antagonists", Exp. Opinion Ther. Patents (2000), 10 (7), 1045-1055).

Thus, the compounds of the invention of formula (I) were subjected to an in vitro affinity assay on the native histamine H$_3$ receptor in an adult rat brain membrane preparation by the specific binding of [$^3$H]-N-α-methylhistamine to this receptor, according to methods described by Korte, A. et al. in Biochem. Biophys. Res. Commun., 168, 979-986 (1990) and by West, R. E. Jr. et al. in Mol. Pharmacol., 38, 610-613 (1990).

The K$_i$ values of the compounds of the invention with regard to the H$_3$ receptors lie between 0.1 nM and 5.0 μM and more particularly 2-(cyclohexylmethyl)-7-[2-(1-methylpyrrolidin-2-yl)ethoxy]-1,2,3,4-tetrahydroisoquinoline (compound 5 of the table) exhibits a K$_i$ of 0.1 nM.

The compounds of the invention of formula (I) were also subjected to a cAMP formation assay on the human histamine H$_3$ receptor transfected into CHO cells by the inhibition of the agonism brought about by the specific binding of R-α-methylhistamine to this receptor, according to the methods described by Lovenberg, T. W. et al. in J. Pharmacol. Exp. Ther., 293, 771-778 (2000).

The IC$_{50}$ values of the compounds of the invention with regard to the H$_3$ receptors lie between 0.1 nM and 5.0 μM.

By way of example, compound 5, included in the table, exhibits an IC$_{50}$<10 nM, use being made of an EIA kit (Amersham) to measure the formation of cAMP on the human histamine H$_3$ receptor transfected into CHO cells by the inhibition of the agonism brought about by the specific binding of R-α-methylhistamine to this receptor.

The compounds according to the invention have a selective activity on the histamine H$_3$ receptor. In fact, the compounds exhibit a K$_i$ of greater than 7.0 μM in the in vitro affinity assay on the native histamine H$_1$ receptor in an adult rat brain membrane preparation by the specific binding of [$^3$H]-pyrilamine to this receptor, according to the method described by Liu Y. Q. et al. in J. Pharmacol. Exp. Ther., 268, 959 (1994).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I):

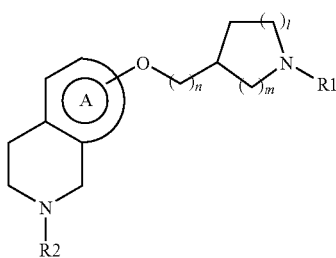

wherein:

represents a 6-membered unsaturated carbocycle with double bonds which is optionally substituted by one or two substituents chosen, independently of one another, from a halogen atom, a hydroxyl, a nitro, cyano, $C_{1-2}$ perhaloalkyl or $C_{1-3}$ alkyl group or a phenyl;

l is 0 to 2;
m is 0 to 2;
wherein the aminocycle comprising —$(C)_l$—, —$(C)_m$— and —NR1- forms a pyrrolidine;
n is 0 to 6;
—$(C)_l$—, —$(C)_m$— and —$(C)_n$— represent, independently of one another, a —$C_{x-z}$— alkylene group, optionally substituted by 1 to 4 substituents chosen from a halogen atom, a hydroxyl, nitro, cyano, amino, $C_{1-2}$ perhaloalkyl or $C_{1-3}$ alkyl group or a phenyl; and when l, m and n are 0, —$(C)_0$— represents a bond;
R1 represents
a hydrogen atom,
a $C_{1-3}$ alkyl group,
a $C_{1-6}$ alkylcarbonyl,
a $C_{1-6}$ alkoxycarbonyl,
it being possible for each to be substituted by a halogen atom, a hydroxyl, $C_{1-3}$ alkoxy, nitro, cyano or amino group or aryl;
a $C_{1-3}$ alkylaryl group,
a monocyclic heteroaryl, and
an aryl;
the aryl and heteroaryl groups optionally being substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a alkylidenedioxy group; and
R2 represents
a $C_{1-6}$ alkyl group or a $C_{3-6}$ cycloalkyl group, each optionally being substituted by 1 to 4 substituents chosen from a halogen atom, a hydroxyl, nitro, cyano, amino, $C_{1-3}$ monoalkylamino, $C_{2-6}$ dialkylamino, $C_{1-2}$ perhaloalkyl, $C_{1-3}$ haloalkyl, $C_{1-3}$ alkoxy or $C_{3-6}$ cycloalkyl group, a monocyclic heteroaryl, a bicyclic heteroaryl or an aryl group itself optionally being substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group,
or a salt thereof.

2. The compound of formula (I) according to claim 1, wherein:

represents a 6-membered unsaturated carbocycle optionally substituted by 1 or 2 substituents chosen, independently of one another, from a halogen atom or a hydroxyl, nitro, cyano, $C_{1-2}$ perhaloalkyl or $C_{1-3}$ alkyl group;
l is 1 or 2;
m is 0 or 1;
wherein the aminocycle comprising —$(C)_l$—, —$(C)_m$— and —NR1- forms a pyrrolidine;
n is 0, 1, 2 or 3;
—$(C)_l$— and —$(C)_m$— form, together with the —NR1- group, an aminocycle bonded via a carbon to the —O—$(C)_n$— group and, when m is 0, —$(C)_0$— represents a bond;
—$(C)_n$— represents a —$C_{0-3}$— alkylene group optionally substituted by 1 to 4 substituents chosen from a halogen atom or a hydroxyl, nitro, cyano, amino or $C_{1-2}$ perhaloalkyl group; and, when n is 0, —$(C)_0$— represents a bond; and
R1 represents
a hydrogen atom,
a $C_{1-3}$ alkyl group,
a $C_{1-6}$ alkylcarbonyl,
a $C_{1-6}$ alkoxycarbonyl;
$C_{1-3}$ alkylaryl,
a heteroaryl,
an aryl group;
the aryl and heteroaryl groups optionally being substituted by 1 to 4 substituents chosen from a halogen atom or a hydroxyl, cyano, amino, $C_{1-3}$ monoalkylamino, $C_{1-3}$ alkyl, $C_{1-2}$ perhaloalkyl, $C_{1-3}$ haloalkyl, $C_{1-3}$ alkoxy or $C_{1-3}$ alkylidenedioxy group,
or a salt thereof.

3. The compound of formula (I) according to claim 2, wherein the aminocycle of which —$(C)_l$—, —$(C)_m$— and —NR1- form part and which is bonded via a carbon to the —O—$(C)_n$— group is:

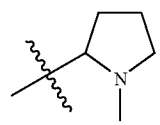

and wherein:
R2 represents
a $C_{1-4}$ alkyl or $C_{5-6}$ cycloalkyl group, each being optionally substituted by 1 to 4 substituents chosen from a phenyl, a monocyclic heteroaryl, a bicyclic heteroaryl or a $C_{3-6}$ cycloalkyl, $C_{1-2}$ perhaloalkyl, $C_{1-3}$ haloalkyl or $C_{1-3}$ alkoxy group; the phenyl and the heteroaryl optionally being substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group, or a salt thereof.

4. The compound of formula (I) according to claim 1, wherein the unsaturated carbocycle with double bonds is a phenyl, or a salt thereof.

5. The compound of formula (I) according to claim 1, wherein R1 is chosen from benzyloxycarbonyl, benzyl, phenethyl, thienyl, furyl, pyrrolyl, phenyl or naphthyl, or a salt thereof.

6. The compound of formula (I) according to claim 1, wherein R2 represents a $C_{1-4}$ alkyl or $C_{5-6}$ cycloalkyl group, each optionally being substituted by a monocyclic heteroaryl chosen from thienyl, furyl, pyrrolyl, benzotriazolyl, or an aryl chosen from phenyl or naphthyl, or a salt thereof.

7. The compound according to claim 1, which is selected from the group consisting of:
2-isobutyl-7-[2-(1-methylpyrrolidin-2-yl)ethoxy]-1,2,3,4-tetrahydroisoquinoline;
2-(3-methylbutyl)-7-[2-(1-methylpyrrolidin-2-yl)ethoxy]-1,2,3,4-tetrahydroisoquinoline;
2-(cyclohexylmethyl)-7-[2-(1-methylpyrrolidin-2-yl)ethoxy]-1,2,3,4-tetrahydroisoquinoline;
2-(cyclohexylmethyl)-7-{2-[(2R)-1-methylpyrrolidin-2-yl]ethoxy}-1,2,3,4-tetrahydroisoquinoline;
2-(cyclohexylmethyl)-7-{2-[(2S)-1-methylpyrrolidin-2-yl]ethoxy}-1,2,3,4-tetrahydroisoquinoline;
2-benzyl-7-[2-(1-methylpyrrolidin-2-yl)ethoxy]-1,2,3,4-tetrahydroisoquinoline;
2-butyl-7-[2-(1-methylpyrrolidin-2-yl)ethoxy]-1,2,3,4-tetrahydroisoquinoline;
7-[2-(1-methylpyrrolidin-2-yl)ethoxy]-2-propyl-1,2,3,4-tetrahydroisoquinoline;

or a salt thereof.

8. A pharmaceutical composition comprising a compound of formula (I) according to claim 1 or a pharmaceutically acceptable salt thereof in combination with at least one pharmaceutically acceptable excipient.

9. A pharmaceutical composition comprising a compound of formula (I) according to claim 2 or a pharmaceutically acceptable salt thereof in combination with at least one pharmaceutically acceptable excipient.

10. A pharmaceutical composition comprising a compound of formula (I) according to claim 3 or a pharmaceutically acceptable salt thereof in combination with at least one pharmaceutically acceptable excipient.

11. A pharmaceutical composition comprising a compound of formula (I) according to claim 4 or a pharmaceutically acceptable salt thereof in combination with at least one pharmaceutically acceptable excipient.

12. A pharmaceutical composition comprising a compound of formula (I) according to claim 5 or a pharmaceutically acceptable salt thereof in combination with at least one pharmaceutically acceptable excipient.

13. A pharmaceutical composition comprising a compound of formula (I) according to claim 6 or a pharmaceutically acceptable salt thereof in combination with at least one pharmaceutically acceptable excipient.

14. A pharmaceutical composition comprising a compound of formula (I) according to claim 7 or a pharmaceutically acceptable salt thereof in combination with at least one pharmaceutically acceptable excipient.

15. A process for the preparation of a compound of formula (I) according to claim 1 comprising:
reacting a compound of formula (II):

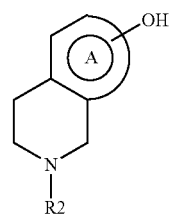

wherein R2 and A are as defined in claim 1, with a compound of formula (III):

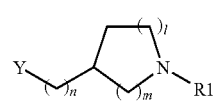

wherein l, m, n, and R1 are as defined in claim 1, and Y represents a halogen atom, hydroxy, or a pseudohalogen selected from the group consisting of mesylate, triflate, tosylate, brosylate and nosylate.

16. A process for the preparation of a compound of formula (I) according to claim 1, in which R1, R2, l, m, n and the A ring are as defined in claim 1 comprising the step according to the following reaction:

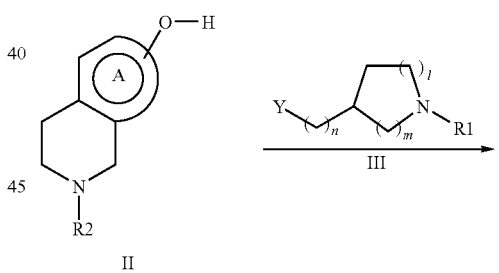

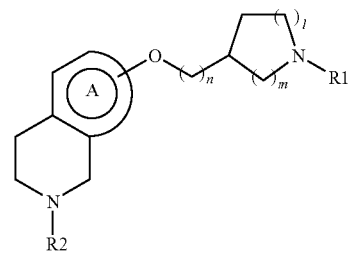

comprising
reacting a phenol of formula (II), wherein R2 and the A ring are as defined in claim 1, under nucleophilic substitution reaction conditions with an amine of formula (III), in which R1, l, m and n are as defined in claim 1 and Y represents a halogen atom, hydroxy, or a "pseudohalogen" selected from the group consisting of mesylate, triflate, tosylate, brosylate and nosylate.

17. The process according to claim 16, wherein the compound of formula (II) is prepared by reductive amination by reacting a secondary amine of formula (IV), in which R2 represents H and Pg is a protecting group:

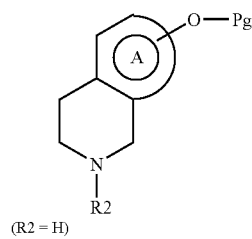

(R2 = H)

with an aldehyde or a ketone of formula (V): (R3R4C(O)), where after reaction, R3 and R4 together with the carbonyl carbon form R2, to form a compound of formula (VI):

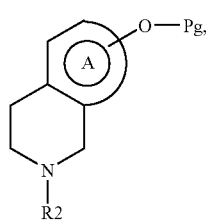

wherein R2 represents a $C_{1-6}$ alkyl group or a $C_{3-6}$ cycloalkyl group, each optionally being substituted by 1 to 4 substituents chosen from a halogen atom, a hydroxyl, nitro, cyano, amino, $C_{1-3}$ monoalkylamino, $C_{2-6}$ dialkylamino, $C_{1-2}$ perhaloalkyl, $C_{1-3}$ haloalkyl, $C_{1-3}$ alkoxy or $C_{3-6}$ cycloalkyl group, a monocyclic heteroaryl, a bicyclic heteroaryl or an aryl group itself optionally substituted by 1 to 4 substituents chosen from a halogen atom, a hydroxyl, nitro, cyano, amino, $C_{1-3}$ monoalkylamino, $C_{2-6}$ dialkylamino, $C_{1-3}$ alkyl, $C_{1-2}$ perhaloalkyl, $C_{1-3}$ haloalkyl or $C_{1-3}$ alkoxy group or a $C_{1-3}$ alkylidenedioxy group; and deprotecting the compound of formula VI to form the compound of formula (II).

18. The process according to claim 16, wherein the compound of formula (II) is prepared by nucleophilic substitution by reacting a compound of formula (VIa):

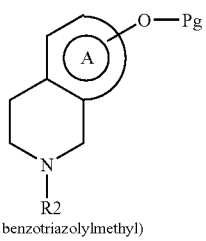

(R2 = benzotriazolylmethyl)

wherein R2 represents a benzotriazolylmethyl group and Pg is a protecting group, with a Grignard reagent of formula (VII) R5MgW, wherein W represents a halogen atom chosen from chlorine, iodine and bromine and R5 represents a $C_{1-5}$ alkyl, $C_{1-2}$ perhaloalkyl, $C_{1-3}$ haloalkyl or $C_{3-6}$ cycloalkyl group, a monocyclic heteroaryl or an aryl group; to form a compound of formula (VIb) wherein R2 is —$CH_2R_5$:

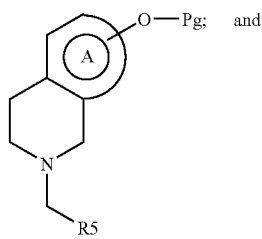

deprotecting the compound of formula VIb to form the compound of formula (II).

* * * * *

UNITED STATES PATENT AND TRADEMARK OFFICE
CERTIFICATE OF CORRECTION

| | |
|---|---|
| PATENT NO. | : 7,678,807 B2 |
| APPLICATION NO. | : 12/122795 |
| DATED | : March 16, 2010 |
| INVENTOR(S) | : Juan Antonio Diaz Martin et al. |

It is certified that error appears in the above-identified patent and that said Letters Patent is hereby corrected as shown below:

On the Title page, in field (56), in column 1, under "Other Publications", line 1, delete "Delvivery" and insert -- Delivery --, therefor.

In column 25, line 63, in claim 1, before "alkylidenedioxy" insert -- $C_{1-3}$ --.

Signed and Sealed this
Twenty-second Day of February, 2011

David J. Kappos
*Director of the United States Patent and Trademark Office*